United States Patent [19]
Peyman

[11] Patent Number: 5,713,844
[45] Date of Patent: Feb. 3, 1998

[54] DEVICE AND METHOD FOR REGULATING INTRAOCULAR PRESSURE

[76] Inventor: Gholam A. Peyman, 8654 Pontchartrain Blvd., Apartment 1, New Orlean, La. 70124

[21] Appl. No.: 781,407

[22] Filed: Jan. 10, 1997

[51] Int. Cl.⁶ .................................................. A61M 5/00
[52] U.S. Cl. ........................................................... 604/9
[58] Field of Search ........................ 604/8–10, 294; 623/4

[56] References Cited

U.S. PATENT DOCUMENTS

| | | | |
|---|---|---|---|
| 3,601,128 | 8/1971 | Hakim | 604/9 |
| 4,240,434 | 12/1980 | Newkirk. | |
| 4,428,746 | 1/1984 | Mendez | 604/8 |
| 4,521,210 | 6/1985 | Wong | 604/8 |
| 4,554,918 | 11/1985 | White | 604/10 |
| 4,750,901 | 6/1988 | Molteno | 604/8 |
| 4,826,478 | 5/1989 | Schocket | 604/8 |
| 4,936,825 | 6/1990 | Ungerleider | 604/8 |
| 4,968,296 | 11/1990 | Ritch et al. | 604/8 |
| 5,073,163 | 12/1991 | Lippman | 604/9 |
| 5,092,837 | 3/1992 | Ritch et al. | 604/8 |
| 5,178,604 | 1/1993 | Baerveldt et al. | 604/8 |
| 5,338,291 | 8/1994 | Speckman et al. | 604/9 |
| 5,346,464 | 9/1994 | Camras | 604/9 |
| 5,370,607 | 12/1994 | Memmen | 604/8 |
| 5,397,300 | 3/1995 | Baerveldt et al. | 604/8 |
| 5,433,701 | 7/1995 | Rubinstein | 604/8 |
| 5,454,796 | 10/1995 | Krupin | 604/294 |
| 5,476,445 | 12/1995 | Baerveldt et al. | 604/8 |
| 5,486,165 | 1/1996 | Stegmann | 604/8 X |

*Primary Examiner*—Mary Beth Jones
*Attorney, Agent, or Firm*—Wood, Herron & Evans, L.L.P.

[57] ABSTRACT

A device and method to regulate intraocular pressure. An interior tube, with one terminus attached to a reservoir and the other terminus left open, is encased along its length by an expandable exterior tube with closed ends. The interior tube wall is flexible such that external pressure reduces the diameter of the interior tube. The device is implanted in an eye with the tubes positioned under the conjunctiva, the open terminus of the interior tube in fluid communication with the anterior chamber of the eye, and the reservoir attached to the eye. The exterior tube can be accessed for filling with fluid. The filled exterior tube exerts pressure on the interior tube wall and reduces the diameter of the interior tube, which in turn reduces or restricts outflow of aqueous fluid from the anterior chamber. The filled exterior tube also substantially occupies the incision site and physically prevents leakage of aqueous fluid.

16 Claims, 1 Drawing Sheet

DEVICE AND METHOD FOR REGULATING INTRAOCULAR PRESSURE

BACKGROUND OF THE INVENTION

Glaucoma is a pathological condition resulting from a sustained increase in the normal intraocular pressure of approximately 18 mm Hg. The increase in pressure occurs when aqueous fluid either is not properly drained from, or is overproduced and accumulates in, the eye. Left untreated, the sustained increase in pressure may compress the optic nerve, resulting in severe consequences such as impaired vision or even blindness. Glaucoma is treatable, however, either pharmacologically, surgically, or by implanting devices to drain excess aqueous fluid from the anterior chamber of the eye. Because pharmacologic treatments may be expensive and at times ineffective, and because surgical procedures often fail and may have to be repeated, implants to drain the excess fluid are an attractive option for some patients.

Current methods of relieving intraocular pressure by surgical implantation of a drainage device, however, suffer from two major drawbacks: (1) aqueous fluid leakage around the implant following surgery, and (2) inability to regulate the volume of fluid drained from the anterior chamber of the eye. After surgical implantation of a drainage device, a period of time from one to eight weeks is normally required for the tissue to seal the wound. During this period, aqueous fluid continues to leak into surrounding tissues until sufficient scar tissue forms to seal the incision site. If the volume of aqueous fluid that is lost exceeds the volume that is physiologically required, hypotonicity (low intraocular pressure) will result with damage to ocular tissues. There are only a few devices disclosed in the prior art that allow the aqueous fluid in the anterior chamber to be actively regulated, rather than merely passively monitored.

One such device that allows regulation of the aqueous fluid in the anterior chamber is disclosed in U.S. Pat. No. 5,454,796. That device consists of a tube, with one end opening into a plate attached to the sclera and the other end opening into the anterior chamber of the eye, containing a check valve that permits aqueous fluid to drain from the anterior chamber at a controlled rate until a predetermined intraocular pressure is reached. Once the pressure falls below this set point, the valve is activated and additional drainage is stopped.

A disadvantage of the '796 device is that it does not prevent leakage of aqueous fluid around the incision site, but instead merely regulates the flow of aqueous fluid inside the tube. An additional disadvantage is that the valve means can malfunction, for example, the valve may prevent aqueous flow out of the anterior chamber when the intraocular pressure falls, but may not reopen once intraocular pressure increase.

A second device, disclosed in U.S. Pat. No. 5,433,701, also employs a valve means to regulate fluid in the anterior chamber of the eye. The device uses a mechanical means for regulating aqueous flow through a plurality of channels. Flow is regulated by physical occlusion, either complete or partial, using a biocompatible body or strand. The degree of occlusion is predetermined and is set at the time the device is implanted. Any change in the flow must then be accomplished by physical means, that is, removal or addition of one or more bodies or strands. An alternative embodiment of the device discloses channels formed from a deformable material for the purpose of facilitating use of the valve means. Additional alternative embodiments use a valve containing an outflow monitor that can selectively increase or decrease the degree of outflow resistance through the channel, and a pump to force aqueous fluid through the channels.

One disadvantage of this device is that, like the '796 device, it does not prevent aqueous fluid from leaking around the incision site, but instead merely provides a means to regulate the aqueous fluid that does leak through the tube. Another disadvantage is that it requires the initial extent of occlusion to be preselected before implantation occurs, thus not allowing the physician to account for an individual patient's response to the surgery. Still another disadvantage of this device is the need for components, such as valves, bodies, strands, or multiple channels, which may be sources of malfunction of the device or sources of physiologic irritation to the patient.

Because of the aforementioned disadvantages, there is a need for a device which both reduces post-implant loss of aqueous fluid, as well as allows for regulation of any fluid that does leak by a minimally invasive procedure. It is also desirable that the device permit the physician to account for interpatient variability in controlling the outflow volume of aqueous fluid.

SUMMARY OF THE INVENTION

This invention is directed to a device and method for regulating intraocular pressure in a mammalian eye. The device is an improvement over prior art in that it addresses the two common problems that occur following an implant, namely, leakage around the incision site and excess loss of aqueous fluid from the anterior chamber. The device reduces aqueous fluid loss by physically occupying much of the space around the incision site and preventing inflow of aqueous into the space. The device also permits the physician to effect individualized, efficient regulation of aqueous fluid outflow from the anterior chamber without resorting to valves, physical occluding materials, or multiple channels that could malfunction or cause irritation in a patient.

Thus, one aspect of the present invention is a physiologically compatible device for regulating intraocular pressure sized and configured for attachment to an afflicted eye. The device consists of a reservoir for receiving aqueous outflow from the anterior chamber of the eye, an interior tube with one terminus in fluid communication with the anterior chamber and the other terminus opening into the reservoir, and an expandable exterior tube with closed ends encasing the interior tube along its length but not at its termini, and capable of receiving exogenous fluid. In one embodiment, the reservoir may be attached to the sclera. The interior tube is configured with a so-called "weak spot"due to either weakening of the wall of the interior tube at that site, or a different, more elastic composition of the interior tube at that site. The interior tube is encased along its length, but not so that its termini are occluded, by an expandable exterior tube. Upon introduction of exogenous fluid into the space between the interior and exterior tubes, the pressure exerted upon the interior tube wall causes the interior tube wall to crimp at its weak spot. This decreases the diameter of the interior tube wall, leading to a concomitant decrease, or even total occlusion, of aqueous fluid flow from the anterior chamber to the reservoir.

Another aspect of the present invention is a process for regulating the abnormally low intraocular pressure that often results after a drainage device is implanted. If abnormally low intraocular pressure is detected, a predetermined volume of exogenous fluid is inserted into the space between the interior and exterior tubes. This exogenous fluid exerts pressure upon the weak spot in the interior tube wall. Depending upon the degree of pressure exerted, the diameter of the interior tube is reduced either partially or completely. If partially reduced, aqueous flow from the anterior chamber through the interior tube is slowed. If completely reduced, aqueous flow from the anterior chamber through the interior tube is stopped.

In addition to regulating aqueous flow, the device helps to minimize leakage of aqueous fluid around the incision through which the drainage device was inserted. Upon filling the exterior tube with exogenous fluid, the exterior tube expands to occupy substantially the entire space around the incision site. This physically prevents aqueous fluid from leaking into the area of the incision site.

The above and other objects and advantages of the present invention will be made apparent from the accompanying drawings and the description thereof.

DETAILED DESCRIPTION

Figure 1:
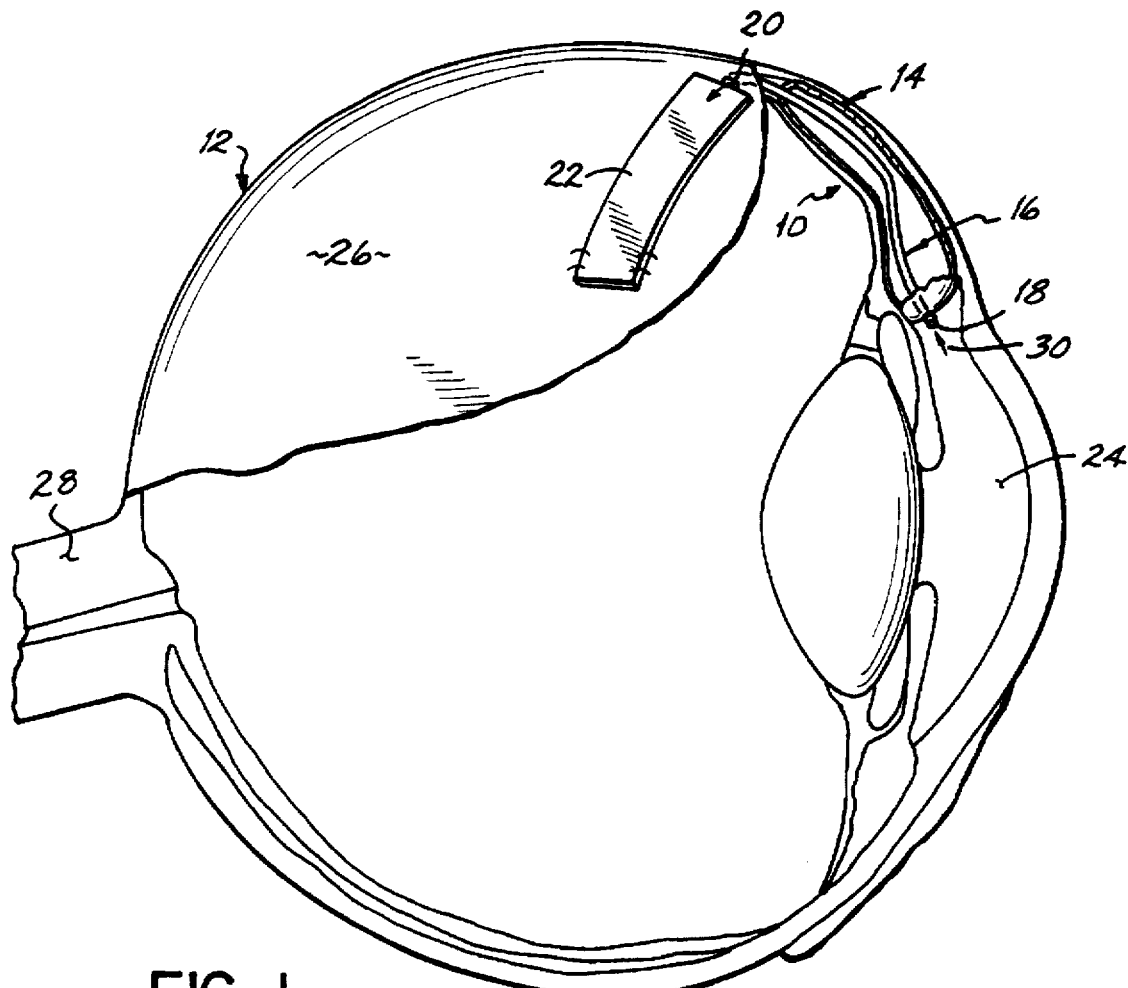
FIG. 1 is a partial cross-section of the present invention in place in an eye.

FIG. 1 shows a device 10, used to regulate intraocular pressure, that has been implanted in a mammalian eye 12. The device 10 consists of a tube-within- a-tube system, with an exterior tube 14 forming a closed chamber around the length of an interior tube 16. The interior tube 16 has one terminus 18 that is open while the other terminus 20 is attached to a reservoir 22. The interior tube is composed of a semi-flexible polymer, which can be a silicone elastomer, polypropylene, or thermoplastic elastomer. The exterior tube is composed of a semi-solid polymer which can be latex rubber.

In use, the device 10 is positioned within an eye 12 so that the open terminus 18 of the interior tube 16 is situated proximally and opens into the anterior chamber 24 of an eye 12, and the distal terminus 20 of the interior tube 16 opens into the reservoir 22. In one embodiment, the reservoir may be attached to the sclera 26.

Aqueous fluid, which serves to maintain intraocular pressure, normally fills the anterior chamber 24 of the eye 12. When excess aqueous accumulates, the resultant increase in pressure can damage the optic nerve 28. Over a period of time this can have severe consequences such as reduced vision or even blindness.

Implantation of the device 10 facilitates aqueous flow out of the anterior chamber 24 of the eye 12. Aqueous fluid that is produced in the anterior chamber 24 enters the interior tube 16 in the direction of the arrow 30 and flows through the interior tube 16 to the reservoir 22. The reservoir 22 provides a large surface area for absorption of aqueous fluid into the bloodstream, as disclosed in the prior art. The interior tube 16 is encased along its length by a flexible exterior tube 14, which forms a closed system around the length of the interior tube 16 but which does not occlude the termini 18,20 of the interior tube 16.

Figure 2:
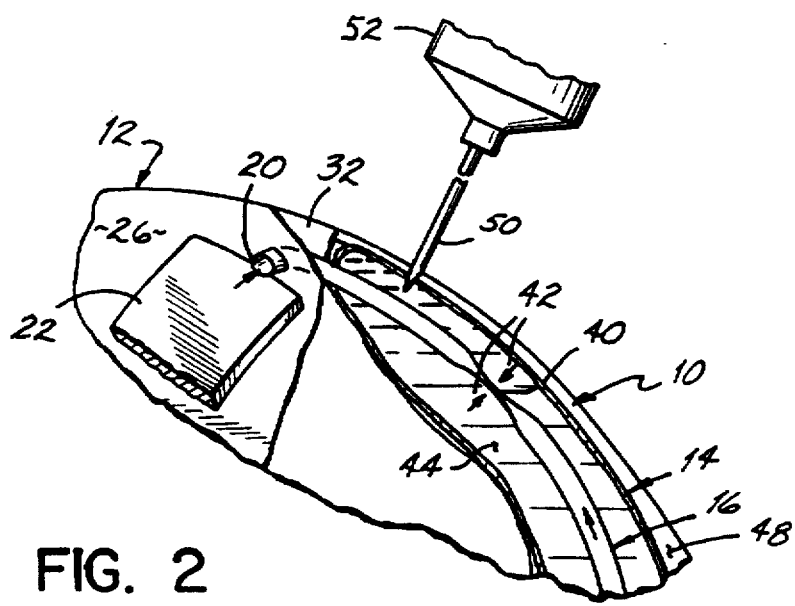
FIG. 2 is an enlarged partial cross-section of the present invention in use in an eye.

FIG. 2 shows the device 10 in use. The device 10 is implanted in the eye 12 so that the exterior and interior tubes 14, 16 are positioned under the conjunctiva 32. When abnormally low intraocular pressure is detected, exogenous fluid 44 is added to the exterior tube 14. The exogenous fluid can be a viscoelastic injectable material. The volume of the exogenous fluid is determined by measuring the intraocular pressure and using a nomogram to correlate volume of the exogenous fluid with the pressure exerted on the interior tube wall. The exogenous fluid 44 exerts pressure 42 on the interior tube 16. Because the interior tube 16 is configured to contain a weak spot 40 in its wall, the pressure inwardly deforms the interior tube 16 at the weak spot 40, thereby reducing the diameter of the interior tube 16 and reducing or completely occluding aqueous flow through the interior tube 16. In addition, the fluid-inflated 44 exterior tube 14 occupies substantially all of an incision site 48, thereby physically preventing aqueous leakage into the site. After a sufficient post-surgical period to allow scar tissue to form, the fluid 44 from the filled exterior tube 14 is drained. In one embodiment, this is accomplished by inserting a needle 50 attached to a syringe 52 to remove the fluid 44 from the exterior tube 14.

The procedure of the present invention is as follows: The device 10 is surgically implanted in an afflicted eye 12 while the patient is under either local or general anesthesia. After recovery, the patient resumes normal activity. Intraocular pressure is routinely monitored at selected intervals. Whenever the intraocular pressure is determined to be outside the desired range, it may be regulated by the following simple procedure: a local anesthetic is administered to the eye, preferably in the form of eye drops, then exogenous fluid 44 is added to the exterior tube 14. In one embodiment, a needle 50 attached to a syringe 52 may be used to add the exogenous fluid 44, which may be a physiologic saline solution.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A physiologically compatible intraocular device for regulating intraocular pressure, comprising:

a reservoir sized and configured for attachment to an eye for receiving aqueous outflow from an anterior chamber of said eye;

an interior tube sized and configured for positioning in said eye with one terminus opening into said anterior chamber and the other terminus opening into said reservoir, said interior tube having a flexible wall for controlling said aqueous outflow from said anterior chamber to said reservoir upon application of pressure to said flexible wall; and an expandable exterior tube having closed ends sized and configured for positioning in said eye and encasing said interior tube along a length of said interior tube, said expandable exterior tube for receiving exogenous fluid to provide said pressure to said interior tube flexible wall, thereby regulating said aqueous fluid flow through said interior tube.

2. The device of claim 1 wherein said pressure is sufficient to reduce said aqueous flow.

3. The device of claim 1 wherein said pressure is sufficient to restrict said aqueous flow.

4. The device of claim 1 wherein said device is sized for positioning said interior and exterior tubes under a conjunctiva.

5. The device of claim 1 wherein said exterior tube is sized and configured for filling with exogenous fluid.

6. The device of claim 1 wherein said exterior tube is sized for accessing with a needle attached to a syringe.

7. The device of claim 1 wherein said interior tube is composed of a semiflexible polymer.

8. The device of claim 1 wherein said interior tube is selected from the group consisting of a silicone elastomer, polypropylene, and thermoplastic elastomer.

9. The device of claim 1 wherein said exterior tube is composed of a semisolid polymer.

10. The device of claim 1 wherein said exterior tube is composed of latex robber.

11. A method for regulating intraocular pressure, comprising:

(A) surgically implanting a device comprising:

(i) a reservoir sized and configured for attachment to an eye for receiving aqueous outflow from an anterior chamber of said eye;

(ii) an interior tube sized and configured for positioning in said eye with one terminus opening into said anterior chamber and the other terminus opening into said reservoir, said interior tube having a flexible wall for controlling said aqueous outflow from said anterior chamber to said reservoir upon application of pressure to said flexible wall; and (iii) an expandable exterior tube having closed ends sized and configured for positioning in said eye and encasing said interior tube along a length of said interior tube, said expandable exterior tube for receiving exogenous fluid to provide said pressure to said interior tube flexible wall, thereby regulating said aqueous fluid flow through said interior tube;

(B) monitoring post-implant intraocular pressure; and (C) regulating said pressure by adding a desired volume of said exogenous fluid to said exterior tube to exert sufficient pressure on said interior tube wall and to expand said exterior tube to substantially occupy an incision site.

12. The method of claim 11 wherein said eye is first anaesthetized.

13. The method of claim 11 wherein said volume of said exogenous fluid is determined by measuring intraocular pressure and using a nomogram to correlate volume of exogenous fluid with pressure exerted on said interior tube wall.

14. The method of claim 11 wherein said exogenous fluid is added using a needle attached to a syringe.

15. The method of claim 11 wherein said exogenous fluid is a physiologic saline solution.

16. The method of claim 11 wherein said exogenous fluid is a viscoelastic injectable material.

* * * * *